United States Patent [19]

Anderson

[11] Patent Number: 5,042,988
[45] Date of Patent: Aug. 27, 1991

[54] COMPOSITIONS CONTAINING NITROANILINE DYES HAVING A CARBAMIDE SUBSTITUENT GROUP

[75] Inventor: James S. Anderson, Danbury, Conn.

[73] Assignee: Clairol Incorporated, New York, N.Y.

[21] Appl. No.: 606,249

[22] Filed: Oct. 31, 1990

[51] Int. Cl.⁵ .................... A61K 7/13; C07C 211/00
[52] U.S. Cl. ............................................ 8/414; 8/405;
8/406; 8/407; 8/408; 8/428; 8/429; 8/435;
564/441
[58] Field of Search ................. 8/405, 406, 407, 408,
8/414, 428, 429, 435; 564/441

[56] References Cited

U.S. PATENT DOCUMENTS 4,337,061  6/1982  Bugaut et al. ............................ 8/405
4,417,896  11/1983  Bugaut et al. ............................ 8/405
4,619,666  10/1986  Rose et al. ............................... 8/414

Primary Examiner—Paul Lieberman
Assistant Examiner—William S. Parks
Attorney, Agent, or Firm—Charles J. Zeller

[57] ABSTRACT

The novel hair dye compositions containing a compound of the formula:

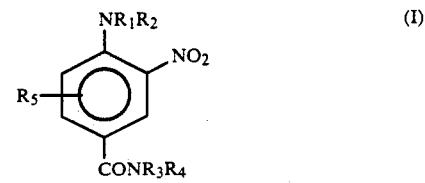

where $R_1$, $R_2$, $R_3$ and $R_4$ which may be identical or different, are hydrogen, alkyl, hydroxyalkyl, polyhydroxyalkyl, alkoxyalkyl, hydroxyalkoxyalkyl aminoalkyl and dialkylaminoalkyl, each alkyl group and each alkoxy group having from about 1 to about 6 carbons and $R_5$ is hydrogen or alkyl containing from about 1 to about 6 carbon atoms are disclosed. More specifically, the present invention concerns the inclusion of such compounds of formula I in hair dye compositions as direct dyes, and especially the novel compound 4-(2-hydroxyethylamino)-3-nitrobenzamide. The compounds, some of which are novel, provide a yellow dye base for the hair dyeing compositions.

8 Claims, No Drawings

COMPOSITIONS CONTAINING NITROANILINE DYES HAVING A CARBAMIDE SUBSTITUENT GROUP

FIELD OF INVENTION

The present invention concerns the novel hair dye composition containing compounds of the formula:

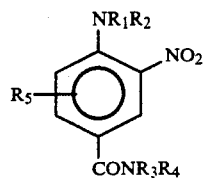

wherein $R_1$, $R_2$, $R_3$ and $R_4$ which may be identical or different, are hydrogen, alkyl, hydroxyalkyl, polyhydroxyalkyl, alkoxyalkyl, hydroxyalkoxyalkyl, aminoalkyl and dialkylaminoalkyl, each alkyl group and each alkoxy group having from about 1 to about 6 carbons and $R_5$ is hydrogen or alkyl containing from about 1 to about 6 carbon atoms. The novel compound 4-(2-hydroxyethylamino)-3-nitrobenzamide, which species provides a yellow dye for the hair dye composition is presently preferred. Several of the compounds useful in the compositions of this invention are novel.

BACKGROUND OF THE INVENTION

Nitro dyes, especially 2-nitroaniline derivatives, have long been used in the hair coloring art, including both oxidative and nonoxidative hair dye compositions. Such compositions typically include two or more hair dyes to provide an acceptable composite coloring effect to the hair. Depending on the shade desired, more or less of a yellow hair dye would be included. Indeed, in the dyeing of hair with a direct dye, it is necessary to provide dyes in admixture, to produce the natural shades desired. Yellow dyes are especially useful to impart blond and other lighter shade to human hair.

A direct yellow dye of the prior art that is characterized by color fastness in the absence of light is:

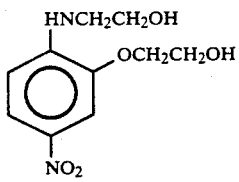

which compound is described in U.S. Pat. Nos. 4,337,061 and 4,417,896. Disadvantageously, the compound (II) has less than desirable light stability.

EP 182,330 discloses the direct dye:

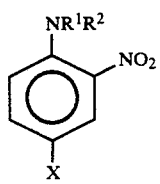

wherein $R^1$ and $R^2$ stand for H, $C_1$-$C_4$ alkyl, $C_2$-$C_4$ monohydroxyalkyl and $C_3$-$C_4$ dihydroxyalkyl, except that $R^1$ and $R^2$ do not simultaneously stand for $C_1$-$C_4$ alkyl radicals, and X is one of the radicals alkyl, monohydroxyalkyl, perfluoralkyl or halogen. Upon variation of the substituent X, the compound provides yellow shades ranging from blue-tinged lemon yellow to pure yellow to orange. Unfortunately, compounds represented by formula III, especially when $R^1$ is $CH_2CH_2OH$; $R^2$ is hydrogen, and X is $CF_3$ have a lower affinity for hair than compounds of formula I when $R_1$ is $CH_2CH_2OH$, and $R_2$, $R_3$, $R_4$ and $R_5$ are all hydrogen. Accordingly, a greater amount of the aforementioned Compound (III) is needed to obtain an equivalent color on hair.

U.S. Pat. No. 4,619,666 describes hair coloring preparations containing as hair dyes, compounds typically of the formula:

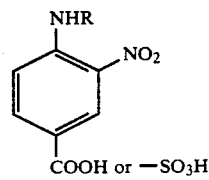

including 4-(2-hydroxyethylamino)-3-nitrobenzoic acid and several additional homologs and analogs of that compound in which R may be hydrogen, $C_1$-$C_4$ alkyl and a number of other substituents. These compounds contain anionic groups which gives them a poor affinity for hair under typical alkaline dyeing conditions.

Copending and commonly owned U.S. application Ser. No. 07/333,528 discloses and claims hair dyes of the formula:

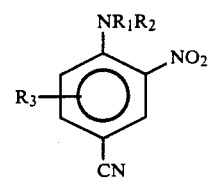

wherein $R_1$ and $R_2$, $R_3$ which may be identical or different, are hydrogen, alkyl, hydroxyalkyl, polyhydroxyalkyl, alkoxyalkyl, hydroxyalkoxyalkyl, aminoalkyl and dialkylaminoalkyl, each alkyl group and each alkoxy group having from about 1 to about 6 carbons, and $R_3$ is a compatible substituent group, for example, hydrogen, alkyl having from about 1 to about 6 carbon atoms and halogen. These compounds, however, may slowly hydrolyze in alkaline formulations. The compounds utilized in the compositions of this invention are not subject to such hydrolysis.

SUMMARY OF THE INVENTION

A primary object of the present invention is to provide yellow direct dyes stable in alkaline formulations and suitable for coloring hair and having good light stability and wash fastness.

Yet another aspect of the present invention is to provide a process for the synthesis of the direct carbamonitroamino dyes of the present invention.

The dyes employed in the compositions of the present invention have the structural formula:

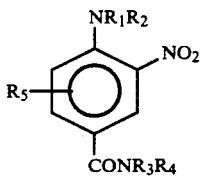

(I)

wherein $R_1$, $R_2$, $R_3$ and $R_4$ which may be identical or different, are hydrogen, alkyl, hydroxyalkyl, polyhydroxyalkyl, alkoxyalkyl, hydroxyalkoxyalkyl, aminoalkyl and dialkylaminoalkyl, each alkyl group and each alkoxy group having from about 1 to about 6 carbons and $R_5$ is hydrogen or alkyl containing from about 1 to about 6 carbon atoms. It has been found that compounds of formula I of the present invention are suitable to color hair and provide above-average light stability and washfastness.

Preferably, $R_1$ is $CH_2CH_2OH$, $CH_2CH_2OCH_2CH_2OH$, or $CH_2CH(OH)CH_2OH$, and $R_2$, $R_3$, $R_4$ and $R_5$ are hydrogen.

As indicated above, certain of the compounds employed in the compositions and the methods of this invention are novel. They are specifically within the broad ambit of this invention. They are represented by the formula:

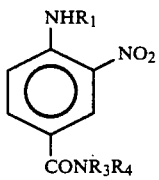

wherein $R_1$, $R_3$ and $R_4$ are as follows:

| $R_1$ | $R_3$ | $R_4$ |
|---|---|---|
| —$CH_2CH_2OH$ | H | H |
| —$CH_2CH_2OH$ | —$CH_2CH_2OH$ | H |
| —$CH_2CH(CH_3)OH$ | H | H |
| —$CH_2CH_2OH$ | —$CH_2CH_2OH$ | —$CH_2CH_2OH$ |
| H | —$CH_2CH_2OH$ | —$CH_2CH_2OH$ |

DETAILED DESCRIPTION OF THE INVENTION

The direct dyes of the present invention are suitable for incorporation in a hair dye composition comprising one or more of the following; solvents, surfactants or surface-active agents, thickeners, antioxidants, preservatives, fragrances, and other constituents typically employed in hair dye compositions. In addition, the dye composition may also contain one or more additional dye components, the admixture of dyes (including at least one dye of the present invention) providing the desired shade. The compositions of the present invention may also contain one or more hair conditioning agents. Such conditioning agents are typically cationic in character and include cationic surface-active agents and cationic polymeric materials. The dyes of the present invention may also be incorporated into an oxidation dye base, to obtain a desired shade.

The constituents includable in the hair dye compositions of the present invention may be selected from amongst a wide variety of such constituents well known to the skilled artisan and are generally employed within the weight ranges tabulated below.

TABLE I

| Constituent | Broad Range Wt. % | Usual Range Wt. % |
|---|---|---|
| Antioxidant | 0-1 | 0.01-0.3 |
| Dye (I) | 0.001-5 | 0.01-1 |
| Other dyes | 0-10 | 0.01-4 |
| Surfactants | 0-25 | 0.1-5 |
| Thickening agents | 0-20 | 0.1-5 |
| Nonaqueous solvents | 0-40 | 1-10 |
| pH Modifiers | 0-20 | 0.05-5 |
| Fragrance | 0-5 | 0.05-1 |
| Water | <<< Q.S. 100% >>> | |

The compounds of this invention can be synthesized by any of a number of reactions well known to those skilled in the art. They can, for example be synthesized from the corresponding cyano compounds by hydrolysis. They may also be prepared from the corresponding benzoic acid derivative by conversion to an acid halide, suitably an acid chloride followed by reaction with ammonia or a selected amine. Alternatively, they may be prepared from 4-chloro-3-nitrobenzamide by reaction with a selected amine such as 2-aminoethanol.

Specific syntheses of a compound of the invention is illustrated by the following non-limiting example.

EXAMPLE 1

4-(2-Hydroxyethylamino)-3-Nitrobenzamide

Add 6.0 g (0.03 moles) 4-chloro-3-nitrobenzamide to 60 ml 2-aminoethanol and stir at ambient temperature. When TLC (silica support; 9:1 $CHCl_3$:MeOH eluent) shows no starting material, ca. 3 hrs., pour onto ice. Filter, wash (3×15 ml) with cold $H_2O$, and recrystallize from MeOH/IPA. Yield is 4.5 g (66%) of orange crystals.

MR (DMSO-$d_6$): 8.7(d,1H), 8.5(t,1H), 8.2(m,2H), 7.36(s,1H), 7.1 (d,1H), 5.1(t,1H), 3.7(m,2H), 3.5(m,2H).

MS: M+225

UV/Vis(MeOH): $\lambda max=415$ nm, $\epsilon=5030$

The absorbance maximum and molar extinction coefficient of 4-(2-hydroxyethylamino)-3-nitrobenzamide are as follows:

$\lambda max=415$ nm $\epsilon=5030$ $\lambda$ max is the absorbance maxima for the dye, the value shown above being characteristic of a yellow color. Other compounds of the invention have similar absorbance maxima in the yellow range. $\epsilon$ is the molar extinction coefficient and is calculated from the equation a/bc wherein a is the maximum absorbance, b is the path length (cm) and c is the concentration in moles/liter in methanol. The extinction coefficient is a measure of the intensity of color produced by a dye compound.

It is seen from the above values that the preferred compound of the invention has an extremely high extinction coefficient. Thus, it imparts a very intense color to solutions containing same.

In practice, the dyes employed in this invention would most often be used with other dyes. The amounts of each dye used would depend on the lightness or darkness of the desired shade, as well as on the desired tonality.

In carrying out the present invention, any of the benzamide dyes described above or combinations thereof are incorporated in a fluid hair dye vehicle of the type suitable for applying direct-dyeing dyes. A large number of such vehicles are known to those skilled in this art. These may vary from simple aqueous solutions and/or suspensions of the dye to very sophisticated aqueous compositions such as creams, mousses, lotions, pastes, gels, and the like. Often, the compositions of the present invention contain, in addition to the subject dyes herein disclosed, a second dye or a blend of other dyes, nonionic and anionic surfactants, solvents, thickeners, antioxidants, preservatives, fragrances, etc. In these aqueous compositions, the carriers or vehicles may be water or a combination of water with other solvents, e.g., ethanol. The dyes may also be employed in an aerosol system, e.g., an aerosol emulsion system in which the dye is contained in an aqueous phase of the system. See, for example, U.S. Pat. No. 4,021,486 to Halasz, et al.

The benzamide dyes employed in the present invention can be employed to prepare basic, neutral or acidic dye compositions. Furthermore, they may likewise be included in hair dyeing compositions which contain other direct dyeing dyes. A variety of direct dyeing dyes are useful for this purpose is known in the prior art. These include nitro dyes, azo dyes, anthraquinone dyes, etc. By way of illustration, any of the nitro dyes disclosed in the following U.S. patents may be used in conjunction with the present dyes: U.S. Pat. Nos. 2,750,326; 2,750,327; 3,088,877; 3,088,878; 3,088,978; 3,642,423; 3,950,127; 4,125,601; 4,432,769, and 4,337,061.

The pH of the present dye compositions can vary from about 4 to 12 and preferably from 7 to 11.5, and may be obtained by adjustment with a suitable pH modifying agent. The compositions herein may also contain any of a variety of known buffering agents to maintain the pH within a particular range.

When the compositions are to be basic, an alkalizing agent can be employed over a wide range, depending on the dye and particular alkalizing agent employed and the desired pH. Illustratively, the weight percent of the alkalizing agent can vary from zero to about 20%, preferably from about 0.05 to about 5%, and most preferably from about 0.10 to about 2%, by weight of the composition. Any of a wide variety of alkalizing agents can be used to adjust the pH of the present dyeing composition on the basic side. Ammonium hydroxide, because of its freedom from toxicity over a broad concentration range and its economy, is an acceptable alkalizing agent. However, there can be used in place of, or together with, ammonia any other compatible ammonia derivative as an alkalizing agent, such as an alkylamine, e.g., ethylamine, dipropylamine, or triethylamine; an alkanediamine, e.g., 1,3-diaminopropane; an alkanolamine, e.g., monoethanolamine or diethanolamine, triethanolamine, a polyalkylene polyamine, e.g., diethylenetriamine; or a heterocyclic amine, such as morpholine.

The pH of the composition may be adjusted on the acid side with any inorganic or organic acid or acid salt which is compatible with the composition and will not introduce toxicity under its conditions of use. Illustrative of acids or acid salts, there can be mentioned: sulfuric, formic, acetic, oleic, lactic, citric or tartaric acid, or ammonium sulfate, sodium dihydrogen phosphate or potassium bisulfate. Illustratively, the weight percent of the acidifying agent is from zero to about 5%, and preferably from about 0.05 to about 1%.

Together, the alkalizing, acidifying and buffering agents are referred to herein as pH modifiers.

Surface active agents can also be employed in the dyeing compositions of this invention. These can be anionic, nonionic or cationic. By way of examples of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethyl-benzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate; glyceryl monostearate; triethanolamine oleate, sodium salt of palmitic methyl taurine; cetyl pyridinium chloride; lauryl sulfonate; myristyl sulfonate; lauric diethanolamide; polyoxyethylene stearate; ethoxylated oleyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate; the sodium salt of 3-O-diethyl tridecanol-6-sulfate and the like. The quantity of surface active agent in weight percent can vary over a wide range, such as from about 0.05% to 15% and preferably from about 0.10 to 5% by weight of the composition.

A thickening agent may also be incorporated in the dyeing composition of this invention which may be one or several of those commonly used in hair dyeing. These are exemplified by such products as sodium alginate or gum arabic, or cellulose derivatives, such as methylcellulose, e.g., Methocel 60 HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite. The quantity of this thickening agent can also vary over a wide range, such as that of from about 0.1 to 20%. Ordinarily it will range from about 0.5 to 5% by weight of the composition. The viscosity of the composition may vary from about 1 cp to about 100,000 cps. For a typical lotion formulation, composition viscosity is between about 100 cps to about 10,000 cps.

It may also be useful to incorporate an antioxidant in the present dye compositions. A variety of antioxidants are known in the prior art which would be useful for this purpose. Among these mention may be made of the inorganic sulfites, e.g., sodium sulfite, thioglycollic acid and other mercaptans, butylated hydroxytoluene (BHT), sodium dithionite, various forms of ascorbic acid and its derivatives, e.g., sodium ascorbate, erythorbic acid, ascorbyl palmitate, ascorbyl laurate, etc. The quantity of antioxidant when in use can vary appreciably. However, this will, in general, be of the order of about 0.001 to 1% by weight.

The benzamide dyes are incorporated in compositions of this invention in tinctorially effective quantities, i.e., in concentrations which are adequate to color the hair. These quantities can vary over a wide range, but ordinarily they will constitute from about 0.001 to greater than about 5%, e.g., 10% by weight of the composition. However, preferably it will comprise from about 0.001 to about 2% by weight of the composition.

The major constituent of the composition employed is usually water, and the amount can vary over a wide range dependent in large measure on the quantity of other additives. Thus, the water content can be as little as 10%, but preferably will be from about 70 to 99% by weight of the hair dye composition.

The dyeing compositions of this invention are preferably aqueous compositions. The term aqueous composition is used herein in its usual generic sense as embracing any water-containing composition useful for the present purposes. This includes true solutions of the dye in an aqueous medium, either alone or in conjunction with other materials, which are also dissolved or dispersed in the aqueous medium. The term aqueous composition also encompasses any mixture of dye with the aqueous medium either alone or together with other ingredients. The dye may be colloidally dispersed in the medium or may merely be intimately mixed therein. Moreover, the aqueous medium may comprise water or water and an additional or auxilliary solvent. The latter may be employed as a common solvent to enhance the solubility of the dye or some other organic material. Other auxiliary solvents which may be used for this purpose include ethanol, carbitol, isopropanol, propylene glycol, ethylene glycol, diethylene glycol, diethylene glycol monoethyl ether, glycerine, etc.

The benzamide dye and any of the surface active agents, thickening agents, and combinations thereof set forth above may be used in the proportions specified in Table I.

The aqueous dyeing compositions of this invention are prepared by conventional methods used in the hair dyeing art. Thus, they can be prepared by dissolving or suspending the dye in water in the desired concentrations. Water miscible organic solvents, e.g., ethanol, can be employed to facilitate solutions of the dye. In this event, the dye can be dissolved first in the solvent and this solution is then diluted with water. The dispersion of the various ingredients can also be facilitated by heating the composition at temperatures varying from 40° C. to 110° C., either before dilution with water or afterwards.

These compositions can be applied to hair by the conventional techniques used in this art. Illustratively, when applied to living hair on the human head, the compositions can be applied to the hair with a brush, sponge, or other means of contact, such as pouring the composition directly onto the hair until saturated. The reaction time or time of contact of the dyeing composition with the hair is not critical and can vary over a wide range used in the hair dyeing art, such as periods of about 5 minutes to about 2 hours. Preferably, a period of from about 5 minutes to about 60 minutes is utilized, and most often a period of 15 to 45 minutes.

The dyeing temperature can vary over wide limits as is conventional in the art. Thus, the dyeing temperature can vary from about room temperature, e.g., about 20° to about 50° C., and preferably from about 20° to about 45° C. At the end of the time period, the composition is rinsed from the hair with water, although a shampoo or a weak acid solution may be employed.

Hunter Tristimulus values were determined to establish the efficacy of 4-(2-hydroxyethylamino)-3-nitrobenzamide and the corresponding nitrile and benzoic acid analogs for dyeing commercial bleached and blended gray hair tresses. They were soaked for 30 minutes at ambient temperature in dye solutions with a concentration of 0.1% by weight based on the total weight and thereafter rinsed with water and dried.

The dye composition contained the following constituents in Wt. %.

|  | Weight % |
| --- | --- |
| Dye | 0.100 |
| Oleic Acid | 1.405 |
| Lauramide DEA | 2.250 |
| Ethoxydiglycol | 6.500 |
| PEG-60 Tallow Amide | 3.105 |
| Hydroxyethylcellulose | 2.100 |
| Aminomethylpropanol | 1.500 |
| BHT | 0.295 |
| Erythorbic acid | 0.045 |
| Fragrance | 0.213 |
| Water | q.s 100 |
|  | 100% |

The Hunter Tristimulus values of the dyed hair tresses are recorded in Table II below.

TABLE II

|  | Blended Grey | | | Commercial Bleached | | |
| --- | --- | --- | --- | --- | --- | --- |
|  | L | a | b | L | a | b |
| Benzamide Cpd. | 34.78, | −1.68, | 12.24 | 63.18, | −2.73, | 32.28 |
| Benzonitrile Cpd. | 33.94, | −0.91, | 8.74 | 64.44, | −2.47, | 25.46 |
| Benzoic Acid Cpd. | 34.39, | 0.09, | 6.85 | 63.79, | −0.10, | 18.98 |

In the Hunter Tristimulus System, L is a measure of lightness and darkness, that is, the depth of the color of the hair tress. The lower the value of L, the darker the color.

A decrease in the value of L indicates a darkening of the hair tress. In the case of bleached and blended gray hair, a lowering of L shows deposition of hair dye on the tress.

The a value is a measure of the greenness or redness of the hair's color. As the a value increases, the hair has a more prominent red tonality. A lowering in the a value results in greener shades. The data in Table II shows that the benzamide dye (Ia) provides improved green nuances to the hair tress.

The value of b is a measure of the blueness or yellowness of the hair color. As the b value increases, the hair tress is more yellow. It is seen that the tresses dyed with the benzamide dye of this invention manifest a substantial increase in the value of b compared to the benzonitrile and benzoic acid analogs.

It will be observed that although there is no appreciable change in the L values of the compounds listed and very little change in the a values, there is a significant change in the b value of the benzamide compound compared to the nitrile and acid compounds. This increase in the yellow value is most unexpected, especially when the modest changes in L and a values are considered. Similar results are observed with other compounds employed in the practice of this invention, and it is these unexpected and unpredictable changes in b values which makes the compounds of this invention so valuable in hair dye compositions.

I claim:

1. A hair dye composition comprising of least one surface active agent and/or thickening agent and at least 0.001% by weight of a compound having the structure:

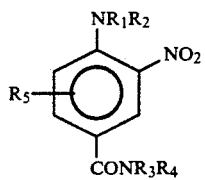

wherein $R_1$, $R_2$, $R_3$ and $R_4$ which may be identical or different, are hydrogen, alkyl, hydroxyalkyl, polyhydroxyalkyl, alkoxyalkyl, hydroxyalkoxyalkyl aminoalkyl and dialkylaminoalkyl, each alkyl group and each alkoxy group having from about 1 to about 6 carbons and $R_5$ is hydrogen or an alkyl group containing from about 1 to about 6 carbon atoms.

2. The composition of claim 1 whereby $R_1$ is hydrogen.

3. The composition of claim 2 wherein $R_2$ is hydroxyalkyl of from 2 to 4 carbons, and $R_3$ is hydrogen.

4. The composition of claim 3 wherein the compound is 4-(2-hydroxyethyl-amino)-3-nitrobenzamide.

5. The hair dye composition of claim 1, 2, 3 or 4 further comprising one or more of the following: surface-active agents in an amount between 0.05% to about 25%, thickening agents in an amount between 0.01% to about 20%, nonaqueous solvents in an amount up to about 40%, pH modifiers in an amount up to about 20%, and fragrance in an amount up to about 5%.

6. The hair dye composition of claim 1, 2, 3 or 4 further comprising one or more additional dyes, said other dyes being in an amount of from about 0.01 to about 10% by weight of the composition.

7. A method of dyeing hair comprising the step of applying to the hair an aqueous composition of claim 1.

8. The method of claim 7 wherein the dye is 4-(2-hydroxyethylamino)-3-nitrobenzamide.

* * * * *